United States Patent [19]  [11]  4,439,545
Aspisi et al.  [45]  Mar. 27, 1984

[54] ACRYLIC COPOLYMERS OF N-ACRYLOYLPOLYMETHYLENEIMINES OR N-ACRYLOYLDIALKYLAMIDES, N,N'-ACRYLOYLDIAMINOALCANES AND N-ACRYLOYLAMINOACIDS (OR ESTERS) THEIR PREPARATION AND USE AS CATION EXCHANGERS

[75] Inventors: Christian Aspisi, Boulbon; Bernard Calas, Saint Gely du Fesc; Jacques Daunis, Montpellier; Michel Follet, Aramon; Robert Jacquier; Joseph Parello, both of Montpellier, all of France

[73] Assignee: Societe d "Expansion Scientifique "Expansia", Paris, France

[21] Appl. No.: 440,441

[22] Filed: Nov. 10, 1982

[30] Foreign Application Priority Data

Nov. 19, 1981 [GB] United Kingdom ................. 8134861

[51] Int. Cl.³ .................... B01J 39/20; C08F 220/58; C08F 220/60
[52] U.S. Cl. ..................................... 521/32; 526/304; 521/32; 521/31
[58] Field of Search ..................... 521/32, 38; 526/304

[56] References Cited

U.S. PATENT DOCUMENTS

| 2,845,408 | 7/1958 | Melamed | 526/364 |
| 3,069,390 | 6/1962 | Kline | 526/364 |
| 3,821,126 | 6/1974 | Yamamoto et al. | 521/32 |
| 3,965,070 | 6/1976 | Wuchter | 521/32 |

OTHER PUBLICATIONS

International Journal of Peptide and Protein Research, vol. 15(4), 1980, pp. 331–334 Stahl et al.

Primary Examiner—Joseph L. Schofer
Assistant Examiner—Peter F. Kulkosky
Attorney, Agent, or Firm—Eyre, Mann, Lucas & Just

[57] ABSTRACT

The invention relates to new reticulated statistic acrylic copolymers that may be used in a very wide range of solvents (water, methylene chloride, chloroform, methanol, ethanol, dimethylformamide, pyridine,) stable between pH 1 and pH 14, to preparation process thereof and to their use in ion exchange chromatography.

7 Claims, No Drawings

ACRYLIC COPOLYMERS OF N-ACRYLOYLPOLYMETHYLENEIMINES OR N-ACRYLOYLDIALKYLAMIDES, N,N'-ACRYLOYLDIAMINOALCANES AND N-ACRYLOYLAMINOACIDS (OR ESTERS) THEIR PREPARATION AND USE AS CATION EXCHANGERS

This invention relates to new reticulated statistic acrylic copolymers, usable in a very wide range of solvents (water, methylene chloride, chloroform, methanol, ethanol, dimethylformamide, pyridine, etc. . . . ), their preparation process and their use in ion exchange chromatography.

The ion exchange chromatography technique involves an insoluble support (matrix), upon which are fixed ionizing groups complexed with ions of opposite sign. These ions may be exchanged with other ions of the same sign, contained in a mobile phase which is placed in contact with the matrix. Depending upon whether the fixed groups are acidic or alkaline, the resin will be named a cation or an anion exchanger.

This technique is applicable to the separation of various constituents of a liquid mixture. Non-ionized molecules will be eluted first and ionized molecules ones will be more or less retained depending on the extent of ionic interaction with the matrix.

This invention relates more particularly to new copolymers, usable as cation exchangers.

Several acrylic or methacrylic resins, comprising carboxylic acid groups are known as ion exchange chromatography supports (cation exchangers); they are generally obtained from non-functional polymers, prepared by radical copolymerization of derivatives of acrylic or methacrylic acid, with a reticulation agent (linker), which may be either methylene-bis-acrylamide N,N'-diacryloyldiaminomethane, (abbreviation MBA), or divinylbenzene.

In most cases, the acidic functions are then introduced on the matrix after polymerization by chemical modification. These reactions are difficult to control and may lead to non homogeneously functionalized products (hydrolysis of the matrix or of the reticulation agent).

Thus, the copolymer of acrylamide and methylene-bis-acrylamide (sold under the trade name of BIOGEL P, belonging to BIORAD Laboratories) gives, after partial hydrolysis by sodium hydroxide, the support sold under the trade name BIOGEL 70 (INMAN and DINTZIS, Biochemistry, 1969, 8, 4074).

The chemical structure of these resins (formula below) shows that the carboxylic function is adjacent to the polymer chain. Consequently, steric hindrances may affect the reaction of the acidic group of the resin, when large molecules are involved.

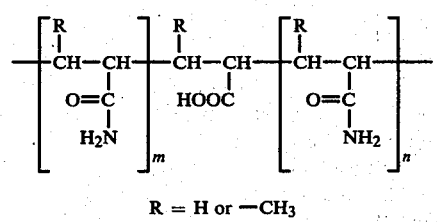

R = H or —CH₃

The same remark applier to other resins, like the ones sold under the trade name TRISACRYL, belonging to PHARMINDUSTRIE (French patent Nos. 2 378 808 and 2 482 112) and obtained by copolymerization with a functionalized monomer.

In addition, some polyacrylamide resins (BIOGEL, DUOLITE, TRISACRYL, are chemically unstable in an alkaline environment, due to partial hydrolysis of the amide groups to carboxylic groups, a characteristic which limits their applications (INMAN and DINTZIS, quoted above).

Poor mechanical stability of polyacrylamides containing a primary amide function is also to be considered. (SCOUTEN, Affinity Chromatography: bioselective absorption on inert matrices, Wiley, 1981).

Finally, SHEPPARD and COLL. (J.C.S. Perkins Trans I, 1981, p. 529 and 538) describes a resin resulting from the copolymerization of N-acryloyldimethylamide, N,N'-diacryloyl 1,2 diamino ethane and of the methyl ester of N-acryloylsarcosine. However, this support has never been hydrolyzed to a copolymer of N-acryloyldimethylamide, N,N'-diacryloyl 1,2 diamino ethane and N-acryloylsarcosine, to be used as a cation exchanger. If this hydrolysis is performed and the acidic resin thus obtained tested in ion exchange chromatography, considerable variations in volume will be noted, in relationship with the ionic strength of the eluent. Thus, working with gradually increasing concentrations of sodium chloride solution results in a decrease of more than 50% in volume of the modified SHEPPARD resin. This gives a considerable lost volume, with an uncertain gradient value and renders the use of this type of resin delicate in cation exchange chromatography.

In order to propose a new type of copolymer, which avoids the disadvantages of those already known, this invention provides a new polyvalent type of reticulated statistic copolymer obtained by the copolymerization of three different monomers, defined as follows:

I. A monomer is defined as the support (matrix) and is an N-acryloylpolymethyleneimine, of the formula:

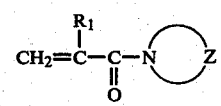

with R₁=H or —CH₃

$$Z = -(CH_2)_{n1}-$$

with n₁=4, 5 or 6 or

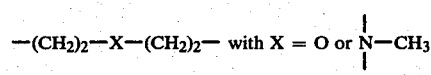

or an N-acryloyldialkylamide, with the formula:

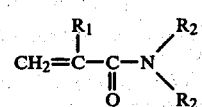

with R₁ having the same meaning above and R₂=—CH₃ or —C₂H₅

II. A monomer defined as the reticulation agent (linker) and which is an N,N'-bisacryloyldiaminoalcane of the formula:

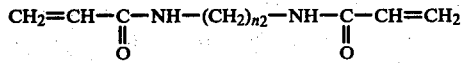   3 with $n_2 = 1$ or 2

III. A monomer defined as the functionalization agent and which is an N-acryloylaminoacid or ester, of the formula:

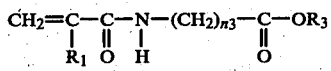   4 with
$R_1$ as above
$R_3$ as $R_1$ and $n_3 = 1, 2, 3$ or 5
or an asymetrical N-acryloylaminoacid (or esters), of the L series, of the formula:

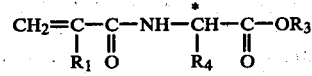   5 with
$R_1$ and $R_3$ having the same meaning as above and $R_4 = -CH_3$ $-CH(CH_3)_2$ $-CH_2(CH_3)_2$

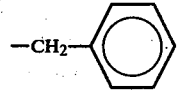

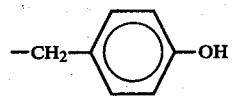

$-CH_2-CH_2-S-CH_3$ $-(CH_2)_4-NH_2$ or, further, the N-acryloyl-L-proline, or its methylic ester. of the formula:

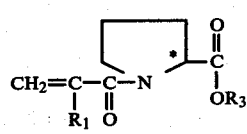   6 with $R_1$ and $R_3$ having the same meaning as above.

The use of monomer N-acryloylpolymethyleneimine 1 or N-acryloyldialkylamide 2, as a matrix which introduces disubstituted amide functions, completely eliminates the formation of the hydrogen bonds. The resins prepared in this way thus swell considerably in a wide range of organic solvents (protic and aprotic) as well as in aqueous buffers of various pH.

The functionalization of supports, using N-acryloylaminoacids (or esters) 4, 5, or 6, makes it possible to modify the chemical nature and the length of the chain between the acidic or ester function and the polymer matrix.

Some monomers used in the matrix are known. They have been described, together with their preparation, in various publications, for instance:

Compounds 1: $R_1 = H$; $Z = -(CH_2)_4-$, $-(CH_2)-_5$; $Z = -(CH_2)_2-O-(CH_2)-_2$
PARROD and Coll., J. Polymer. Sci., 1958, 29, 111.
Compounds 2: $R_1 = H$; $R_2 = -CH_3$
RATCHFORD and Coll., J. Amer. Chem. Soc., 1947, 69, 1911.
$R_1 = H$; $R_2 = -C_2H_5$
U.S. Pat. No. 2,683,741.
Compounds 3: The agents of formula 3 are known:
$n_2 = 1$ (available in Commerce)
$n_2 = 2$
SHEPPARD and Coll., J. Chem. Soc. Perkin I, 1981, 529.

Finally, some functionalization agents of formula 4, 5 or 6, have been described in literature.
Compounds 4: $R_1 = R_3 = H$; $n_3 = 1, 2, 3$ or 5
BROWN and Coll., C.R. Acad. Sci., 1978, 287c, 125.
$R_1 = CH_3$, $R_3 = H$; $n_3 = 1, 2, 3$ or 5
BATZ and KOLDEHOFF, Makromol. Chem., 1976, 177, 683.
WINSTON and KIRCHNER Macromolécules 1978, 11, 89.
LOUPEK and Coll., Bioch. Biophys. Act. 1977, 481, 289.
Compounds 5:

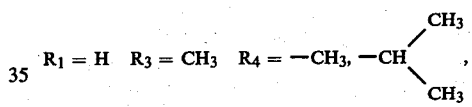

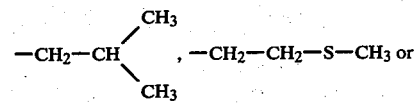

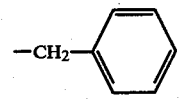

SAKOTA, KOINE NIPPON ZAGAKIN ZASHI 1967, 88 (10), 1087.

The copolymerization of monomers I (matrix) and III (functionalization agents) with a reticulation agent (linker) of type II, leads to resins with physical characteristics suitable for ion exchange chromatography, particularly with regard to the elution rate. With these new copolymers the volume contractions in relationship with the ionic strength of the aqueous eluant never exceed 15%.

Since the polymerization conditions are perfectly controlled and the yields are increased, it is possible to vary the functionalization degree over a wide range. This is achieved by simply modifying the proportion of N-acryloylaminoacid (or ester) (III), in relation to the other two monomers.

The copolymers obtained according to the invention are three-dimensional reticulated statistic copolymers, containing the following, in copolymerized form:

(a) from 30% to 90%, by weight, of a monomer corresponding to an N-acryloylpolymethyleneimine of formula 1, or to an N-acryloyldialkylamide of formula 2;

(b) from 2% to 50% by weight, of a monomer corresponding to an N,N'-diacryloyldiaminoalcane of formula 3 and (c) from 2% to 65%, by weight, of a monomer corresponding to an acryloylaminoacid or ester, racemic of formula 4, or optically active of formula 5 or 6.

The copolymers of the invention contain preferably:
from 70% to 90% monomer I (matrix) corresponding to formula 1 or 2;
from 3% to 10% of monomer II (reticulation agent), corresponding to formula 3;
from 10% to 20% of monomer III (functionalization agent), corresponding to formula 4, 5 or 6.

Supports have been prepared, containing from 0.2 to 10 milliequivalents in carboxylic group, per gram of dry support (directly or after saponification) and it was noted that no hydrolysis of the ester function occurs during polymerization.

Copolymers in acidic form are chemically stable in a clearly acidic or alkaline environment. Treatments for several days in hydrochloric acid or NaOH solutions 0.5 M and 1 M, at room temperature, showed that no hydrolysis, even partial, occurred.

This is due to the presence of a relatively bulky secondary amide, on the monomer forming the matrix, which is much more stable than the primary amides generally used and allows our supports to be used over a very wide range of pH (1 to 14).

The resins obtained show a pKa value between 4.5 and 5.0.

These copolymers are thermally stable: for instance, heating to $+90°$ C. for 12 hours under reduced pressure (0.1 mm of Hg) resulted in no modification.

These supports present also an excellent mechanical stability: after a mechanical agitation for several days, no fine particles formed (no turbidity in the supernatant).

These new reticulated copolymers may be prepared, using known processes, by the radical polymerization of monomers I, II and III.

For instance, the copolymerization may be performed either in block, in an ethylic alcohol-water or dimethyl formamide-water mixture, in a buffer environment (pH=6.0), or in suspension, in water-paraffin or polyvinyl alcohol-water systems. This operation is started by the initiators normally used in radical polymerization, such as N,N,N',N'-tetramethylethylenediamine (TMEDA) + alkaline persulphate,
ammonia persulphate or
azoisobutyronitrile.

3% to 10%, by weight, of reticulation agent is used, together with a quantity of functionalization agent calculated to give 0.2 to 5 milliequivalents of carboxylic acid function per gram of dry resin (directly or after saponification). This is made up to 100%, by weight, by the monomer used for the matrix.

In the case of polymerization in block, the aqueous solution containing the various monomers and the initiator is subjected to a polymerization in homogeneous phase. The transparent gel which is formed is rapidly powdered, washed and filtered. This process gives quantitative yields particularly in beads of uniform size.

Polymerization in suspension gives the resin directly in the form of spherical particles. These are carefully washed and dried. Their size is also very uniform, with diameter between 0.1 mm and 0.25 mm. (measured under microscope).

In this case, an initiator and an emulsifier, are added to the homogeneous solution containing the various monomers.

The mixture is poured into an organic liquid phase, which does not mix with water, and is maintained under stirring. The stirring rate is adjusted to give an emulsion with droplets of the required size. Polymerization is initiated by addition of catalyzing agent (TMEDA) or by gentle heating. The mixture is then agitated until the end of the reaction. The beads of resin thus obtained are washed in a hydrocarbon solvent, then in water, ethanol and with ether. The resin is dried at room temperature under vacuum.

As liquid organic phase may be used, for instance, vegetable oils (soya oil, ground-nut oil, sunflower oil, etc. . . . ) or mineral oils (liquid paraffin, silicone oil).

The emulsifier may be one of the products known commercially as SPAN, ARLACEL or TWEEN, at a concentration of 0.1% to 4% by volume.

The following examples illustrate the various polymerization techniques, together with the various resins claimed.

(A) COPOLYMERIZATION IN BLOCK

EXAMPLE 1

Copolymerization of acryloylpyrrolidine (abbreviation AP), of ethylene bis acrylamide, also known as N,N'-diacryloyl 1,2 diamino ethane (abbreviation EBA) and of N-acryloylglycine methyl ester (abbreviation A Gly O CH$_3$)

0.12 mol (15 g) of AP, $7.8 \cdot 10^{-3}$ mol (1.31 g) of EBA and $1.631 \cdot 10^{-2}$ mol (2.33 g) of N-acryloylglycine methyl ester are dissolved in 34.2 ml of anhydrous ethanol. The clear solution is degassed for 2 minutes in a sonicator. 18 ml of water is added and the solution becomes opaque. The solution is then degassed for a further two minutes and 21.6 ml of phosphate buffer is added (pH 6.0). Degassing is continued until the solution becomes clear again. 3.16 g of ammonia persulphate is then added and is left to dissolve during degassing. 0.53 ml of TMEDA (N,N,N',N'-tetramethyl 1,2 diamino ethane is then added. The temperature then rises quickly and the solution becomes a transparent gel. After 30 minutes, the gel is powdered in a THOMAS grinder and is left to decant in water, in order to eliminate the supernatant fine particles. This operation is repeated after filtering, the resin is successively washed with water, an equal water-acetone mixture, acetone and finally, with diethyl ether. The resulting white powder is dried for 12 hours at $+80°$ C., under reduced pressure (2 mm of Hg). This process gives 13.86 g of white resin. Yield: 74.4%.

To transform this ester resin into an acidic resin, the 13.86 g previously obtained is placed in 300 ml of molar NaOH and this mixture is stirred for two hours at $+25°$ C. After filtering, the resin is successively washed in water, hydrochloric acid (10%), water until neutrality is obtained, molar NaOCH (500 ml), water until neutrality is obtained, hydrochloric acid (10%) and, finally, water until neutrality is again obtained. The resulting resin is dried as before, at $+80°$ C., under reduced pressure (2 mm of Hg). The resin is then filtered to eliminate particles larger than 0,25 mm in diameter and this gives 8.8 g of white powder. The pKa of the OH form is 4.4.

EXAMPLE 2

Copolymerization AP, EBA, methyl ester of N-acryloyl β alanine (abbreviation A β Ala O CH$_3$)

Identical polymerization conditions are used: using 15 g (0.12 mol) of AP, 1.31 g (17.8 10$^{-3}$ mol) of EBA ad 2.55 g (1.631 10$^{-2}$ mol) of methyl ester of N-acryloyl β alanine in 34.2 ml ethanol and with the same quantities of water (18 ml), phosphate buffer (pH 6.0) (21.6 ml), ammonium persulphate (3.16 g) and TMEDA (0.53 ml), after saponification, 9.43 g of dry, white resin is isolated, after filtering, under conditions identical to those described in the paragraph above. The pKa of the OH form is 4.8.

EXAMPLE 3

Copolymerization AP, EBA, methylic ester of N-acryloyl ε-aminocaprioc acid (A ε Cap. O CH$_3$)

The polymerization conditions are identical to those described above, using the following monomers: N-acryloylpyrrolidine (0.12 mol, 15 g), EBA (0.0078 mol, 1.31 g) and methyl N-acryloyl ε aminocaproate (16.31 10$^{-3}$ mol, 3 g). After elimination of fine particles, this gives 13 g (60%) of dry white resin (ester form).

Hydrolysis under the same conditions as before, followed by filtering, gives 10.6 g of dry, white acid resin. The pKa of the OH form is 5.1.

EXAMPLE 4

Copolymerization AP, EBA, methyl ester of N-acryloyl γ amino butyric acid (abbreviation A γ But O CH$_3$)

Using 15 g (0.12 mol) of AP, 1.31 g (7.8 10$^{-3}$ mol) of EBA and 2.76 g (0.01631 mol) of methyl ester of N-acryloyl γ amino butyric acid results in the isolation of 12 g of dry ester resin. After hydrolysis in 300 ml of molar NaOH, and following filtering, this gives 10.8 g of dry acid resin. The pKa of the OH form is 9.0.

EXAMPLE 5

Copolymerization AP, EBA, methyl ester of N-acryloyl L-Leucine (abbreviation A(L)Leu O CH$_3$)

The monomer quantities used are: 15 g of N-acryloylpyrrolidine, 1.31 g of EBA and 3.24 g of methyl ester of N-acryloyl L-Leucine.

The dry ester resin (10.05 g) is subjected to hydrolysis with 300 ml of molar NaOH. Processing as described above, followed by filtering, isolates 8.49 g of acid resin. The pKa of the OH form is 4.8.

EXAMPLE 6

Copolymerization AP, EBA, methyl ester of N-acryloyl L-valine (abbreviation A (L) Val O CH$_3$)

This example uses 15 g of N-acryloylpyrrolidine, 1.31 g of EBA ad 3 g of methyl ester of N-acryloyl L-valine. Standard polymerization and processing gives 9.96 g of dry ester resin. Under the same conditions as those described above, hydrolysis with 300 ml of molar NaOH gives 7.64 g of dry, white acid resin. The pKa of the OH form is 5.0.

EXAMPLE 7

Copolymerization AP, EBA, methyl ester of N-acryloyl L-proline (abbreviation A (L) Pro O CH$_3$)

This example uses 15 g (0.12 mol) of N-acryloylpyrrolidine, 1.31 g (0.0078 mol) of EBA and 2.98 g of methyl ester of N-acryloyl L-proline (16.31 10$^{-3}$ mol). This results in the isolation of 15.03 g (77.7%) of dry resin. Hydrolysis in 300 ml of molar NaOH, followed by filtering, gives 11 g of dry acid resin. The pKa of the OH form is 4.7.

EXAMPLE 8

Copolymerization of acryloylmorpholine (abbreviation AM), EBA and methyl ester of N-acryloyl ε amino caproic acid 5 g (0.0355 mol) of N-acryloylmorpholine, 0.38 g (0.0023 mol) of EBA and 0.995 g (5.38 10$^{-3}$ mol) of N-acryloyl ε amino caproate of methyl are dissolved in 10.4 ml of ethanol. After degassing, the following are added successively, under the conditions described in the first example: 6 ml of water, 7.2 ml of disodium phosphate buffer solution 0.1 M, 1.05 g of ammonia persulphate and 0.176 ml of TMEDA.

Polymerization gives 4,93 g (77.4%) of dry, white resin. Following filtering, hydrolysis gives 2.35 g of dry, white resin. The pKa of the OH form is 5.1.

EXAMPLE 9

Copolymerization AM, EBA, methyl ester of N-acryloyl β alanine

Polymerization is carried out under the same conditions as those described in the paragraph above. The following monomers are used: 5 g (0.355 mol) of N-acryloylmorpholine, 0.38 g (0.023 mol) of EBA ad 0.844 g (5.38 10$^{-3}$ mol) of methyl ester of N-acryloyl β alanine. This results in the isolation of 4.24 g (68.2%) of dry ester resin which, following hydrolysis and filtering, gives 2.18 g of dry acid resin. The pKa of the OH form is 4.8.

EXAMPLE 10

Copolymerization of N,N-dimethylacrylamide (abbreviation ADM), EBA, methyl ester of N-acryloyl ε aminocaproic acid 4.653 g (0.047 mol) of N,N-dimethylacrylamide, 0.51 g (0.003 mol) of EBA and 0.955 g (5.16 10$^{-3}$ mol) of N-acryloyl ε aminocaproate of methyl are dissolved in 13.4 ml of ethyl alcohol. After degassing, the following are added successively, under the conditions described above: 7.05 ml of water, 8.46 ml of disodium phosphate buffer solution 0.1 M, 1.237 g of ammonia persulphate and 0.2 ml of TMEDA. This gives 4.64 g (73%) of white ester resin which, after hydrolysis and filtering, gives 2.44 g of acid resin. The pKa of the OH form is 5.0.

EXAMPLE 11

Copolymerization ADM, EBA, methyl ester of N-acryloyl β alanine

Under the same conditions as those described in the paragraphe above, polymerization is carred out using 4.653 g (0.047 mol) of N-dimethylacrylamide, 0.51 g (0.003 mol) of EBA and 0.81 g (5.16 10$^{-3}$ mol) of the methyl ester of N-acryloyl β alanine. 4.51 g (75.75%) of dry ester resin is formed which, following hydrolysis and filtering, gives 2.36 g of acid resin. The pKa of the OH form is 4.7.

EXAMPLE 12

Copolymerization of N, N-diethylacrylamide (abbreviation ADE), EBA and methyl ester of N-acryloyl β alanine Polymerization is carried out using 2 g of N-diethylacrylamide, 0.17 g of EBA and 0.32 g of the methyl ester of N-acryloyl β alanine in 4.5 ml of ethanol, by successively adding 2.35 ml of water, 2.82 ml of disodium phosphate buffer solution 0.1 m, 0.42 g of ammonia persulphate and 0.067 ml of TMEDA. Following hydrolysis and filtering, this isolates 1.31 g of dry acid resin. The pKa of the OH form is 5.5.

EXAMPLE 13

Copolymerization of ADE, EBA, methyl ester of N-acrylolyl ε aminocaproic acid

Using 6 g of N-diethylacrylamide, 0.5 g of EBA and 1.12 g of methyl ester of N-acryloyl ε aminocaproate, in 18.4 ml of alcohol, and successively adding 7.05 ml of water, 8.46 ml of disodium phosphate buffer solution 0.1 M, 1.24 g of ammonia persulphate and 0.2 ml of TMEDA gives, following hydrolysis and filtering, 4.77 g of dry resin. The pKa of the OH form is 5.42.

EXAMPLE 14

Copolymerization of N-acryloyl hexamethyleneimine, EBA, methyl ester of N-acryloyl β alanine Using 6 g of N-acryloyl hexamethyleneimine, 0.33 g of EBA, 0.65 g of the methyl ester of N-acryloyl β alanine in 8.4 ml of alcohol, the following are added, under the usual conditions: 5.6 ml of water, 6.9 ml of buffer solution, 1.0 of ammonia persulphate and 0.18 ml of TMEDA.

EXAMPLE 15

Copolymerization of N-acryloyl N'-methylpiperazine, EBA, methyl ester of N-acryloyl β alanine 3.0 g of N-acryloyl N'-methylpiperazine chlorydrate, 0.16 g of EBA and 0.3 g of the methyl ester of N-acryloyl β alanine in 4.2 ml of ethanol, are successively treated by 2.8 ml of water, 3.5 ml of buffer solution, 0.5 g of ammonia persulphate and 0.09 ml of TMEDA.

In all these examples, a check was made that the esters obtained are not hydrolyzed during polymerization and that the resins contain no free $CO_2H$.

EXAMPLE 16

Copolymerization of AP, methylenebisacrylamide (MEBA), N-acryloyl β alanine 25 g (0.2 mol) of AP, 2.15 g ($1.3 \ 10^{-2}$ mol) of methylenebisacrylamide and 3.5 g ($2.4 \ 10^{-2}$ mol) of N-acryloyl β alanine are dissolved in 57 ml of absolute ethanol. 30 ml of water, followed by 36 ml of phosphate buffer solution (pH 6.0) are then added. The clear solution is degassed for two minutes. 5.27 g of ammonia persulphate is then added, followed by 0.8 ml of TMEDA. This mixture is allowed to polymerize for 30 minutes. The transparent gel is powdered in a THOMAS grinder, washed in water, then in ethanol, and finally in ether. The resin is dried under vacuum. Yield (27.6 g)

The resin is then filtered and this gives the following sizes of particles:

| | |
|---|---|
| d > 0.25 mm | 4.08 g |
| 0.2 > d > 0.18 | 15.18 g |
| 0.18 > d > 0.16 | 5.37 g |
| 0.16 > d > 0.125 | 0.72 g |

(B) COPOLYMERIZATION IN SUSPENSION

EXAMPLE 17

Copolymerization of methylacryloylmorpholine, EBA, methyl ester N-acryloyl β alanine A mixture of 18.6 g (0.12 mol) of methylacryloylmorpholine, 1.31 g ($7.8 \ 10^{-3}$ mol) of EBA, 2.55 g ($1.63 \ 10^{-2}$ mol) of methyl ester of N-acryloyl β alanine and 100 mg of azoisobutyronitrile is added, under nitrogen, to solution of polyvinyl alcohol (3 g) and water (250 ml) under stirring. This mixture is heated for three hours at +70° C. The polymer is washed in hot water, ethanol, acetone, ethanol and, finally, ether. After drying under reduced pressure (2 mm of Hg), at +80° C., particles are obtained with a diameter of between 0.1 mm and 0.2 mm.

EXAMPLE 18

Copolymerization of methylacryloylmorpholine, EBA, methyl ester of N-acryloyl ε aminocaproic acid Using a mixture of 18.6 g (0.12 mol) of methacryloylmorpholine, 1.31 g ($7.8 \ 10^{-3}$ mol) of EBA, 3.24 g ($1.631 \ 10^{-2}$ mol) of methyl ester of N-acryloyl ε aminocaproic acid and 100 mg of azoisobutyronitrile, processed under the same conditions as those described above, leads to the obtention of 12.6 g of polymer.

EXAMPLE 19

Copolymerization of AP, EBA and methyl ester of N-acryloyl ε alanine 4 g ($3.2 \ 10^{-2}$ mol) of AP, 8 g ($5. \ 10^{-2}$ mol) of N-acryloyl β alanine methyl ester and 1.2 g ($7.14 \ 10^{-3}$ mol) of EBA are dissolved in 50 ml of phosphate buffer solution ($KH_2PO_4$ 0.1 M, diluted to pH 6.0 with NaOH 1 M) and 50 ml of ethanol. 0.6 g of ammonia persulphate and 0.3 ml of SPAN 85 are added to the resulting clear solution. This mixture is placed in 400 ml of liquid paraffin and is then stirred until droplets of the required size are obtained. While stirring, the oxygen is removed from this mixture by bubbling nitrogen through the solution for 20 minutes; 0.92 ml of TMEDA is then added. After 30 minutes' stirring, this mixture is diluted with petrol ether and is then filtered. It is then washed with petrol ether, with water, with an equal water-acetone mixture, with acetone, and finally in ether.

This gives perfectly spherical polymer particles, the size of which may be varied between 0.05 mm and 05 mm, by adjusting the rotation speed. Yield is approximately 90%.

This reaction may also be performed in water, instead of the phosphate buffer solution.

The acid resin sodium salts are easily obtained by washing the polymers in 0.5 solutions of molar NaOH. 30 ml of NaOH solution is used per 1 ml of swollen acid resin. The excess NaOH is eliminated by washing in water, until neutrality is obtained.

The polymer swelling rate has also been measured (Tables 1 and 2). These measurements were carried out on powdered resins.

TABLE 1

VOLUME of 1 g OF RESIN, in ml.

| | Resin | | | | | | | |
|---|---|---|---|---|---|---|---|---|
| | AP + EBA | | AP + EBA | | AP + EBA | | AP + EBA | |
| Medium | A.Gly.OH* | A.Gly.ONa** | A.β.Ala.OH | A.βAla.ONa | A.εCap.OH | A.εCap.ONa | A.Val.OH | A.Val.ONa |
| Dry | 1,9 | 2,2 | 2,2 | 2,1 | 2,2 | 1,6 | 1,8 | 1,5 |
| Water | 11,7 | 22 | 11,0 | 26,2 | 8,8 | 10,5 | 9,2 | 12,0 |
| | (× 6)*** | (× 10)*** | (× 5) | (× 12,5) | (× 4) | (× 10,5) | (× 5) | (× 2) |
| $CH_3OH$ | 10,3 | 19,8 | 12,1 | 20,0 | 8,8 | 10,5 | 9,4 | 12,0 |
| | (× 5,4) | (× 9) | (× 5,5) | (× 9,5) | (× 4) | (× 10,5) | (× 5,2) | (× 8) |
| $C_2H_5OH$ | 12,0 | 12,1 | 14,3 | 18,9 | 12,1 | 9,5 | 13,0 | 13,5 |
| | (× 6,3) | (× 5,5) | (× 6,5) | (× 9) | (× 5,5) | (× 9,5) | (× 7,2) | (× 9) |
| $CH_2Cl_2$ | 13,3 | | 11,0 | | 11 | 9,0 | 13,5 | |
| | (× 7,0) | | (× 5) | | (× 5) | (× 9) | (× 7,5) | |
| $CHCl_3$ | 14,2 | | 12,1 | | 12,1 | 6,0 | 11,7 | |
| | (× 7,5) | | (× 5,5) | | (× 5,5) | (× 6) | (× 6,5) | |
| $C_5H_5N$ | 15,2 | | 18,7 | | 11 | | 19,8 | |
| | (× 8,0) | | (× 8,5) | | (× 5) | | (× 11) | |
| DMF | 10,8 | | 9,9 | | 8,8 | | 8,5 | |
| | (× 5,7) | | (× 4,5) | | (× 4) | | (× 4,7) | |

| | Resin | | | | | |
|---|---|---|---|---|---|---|
| | AP + EBA | | AP + EBA | | AP + EBA | |
| Medium | A.Leu.OH | A.Leu.ONa | A.Pro.OH | A.Pro.ONa | A.Ala.OH | A.Ala.ONa |
| Dry | 1,9 | 2,8 | 3,0 | 2,4 | 2,8 | 2,0 |
| Water | 7,8 | 23,8 | 18,0 | 21,4 | 28 | 26 |
| | (× 4) | (× 2,5) | (× 6) | (× 9) | (× 10) | (× 13) |
| $CH_3OH$ | 11,6 | 22,4 | 15,0 | 16,8 | 22,4 | 16 |
| | (× 6) | (× 8) | (× 5) | (× 7) | (× 8) | (× 8) |
| $C_2H_5OH$ | 10,7 | 22,4 | 18,0 | 19,2 | 22,4 | 14 |
| | (× 5,5) | (× 8) | (× 6) | (× 8) | (× 8) | (× 7) |
| $CH_2Cl_2$ | 11,6 | | 15,0 | | 22,4 | |
| | (× 6) | | (× 5) | | (× 8) | |
| $CHCl_3$ | 11,6 | | 12,0 | | 19,6 | |
| | (× 6) | | (× 4) | | (× 7) | |
| $C_5H_5N$ | 19,4 | | 30,0 | | 16,8 | |
| | (× 10) | | (× 10) | | (× 6) | |
| DMF | 7,8 | | 12,0 | | 14 | |
| | (× 4) | | (× 4) | | (× 5) | |

*Abbreviation A Gly OH corresponds to N—acryloylglycine, and similarly for all the other amino acids, the abbreviation of which contains the "OH" group.
**Abbreviation A Gly ONa corresponds to N—acryloylglycine sodium salt, and similarly for all other amino acid derivatives, the abbreviation of which contains the "ONa" group.
***Number by which the specific volume of the dry resin is multiplied.

TABLE 2

VOLUME OF 1 g OF RESIN, in ml.

| | Resin | | | | | |
|---|---|---|---|---|---|---|
| | ADM + EBA | | ADM + EBA | | AM + EBA | |
| Medium | A.ε.Cap.OH | A.ε.cap.ONa | A.βAla.OH | A.βAla.ONa | A.εcap.OH | A.εcap.ONa |
| Dry | 3,1 | 3,5 | 2,9 | 4,1 | 4,5 | 7,1 |
| Water | 15,5 | 56 | 20,3 | 65,6 | 18 | 78 |
| | (× 5)* | (× 16) | (× 7) | (× 16) | (× 4) | (× 11) |
| $CH_3OH$ | 24,8 | 26,25 | 23,2 | 32,8 | 13,5 | 56,8 |
| | (× 3) | (× 7,5) | (× 8) | (× 8) | (× 3) | (× 8) |
| $C_2H_5OH$ | 21,7 | 21 | 26,1 | 28,7 | 13,5 | 35,5 |
| | (× 7) | (× 6) | (× 9) | (× 7) | (× 3) | (× 5) |
| $CH_2Cl_2$ | 27,9 | | 29 | | 27 | |
| | (× 9) | | (× 10) | | (× 6) | |
| $CHCl_3$ | 24,8 | | 26,1 | | 27 | |
| | (× 8) | | (× 9) | | (× 6) | |
| $C_5H_5N$ | 31, | | 26,1 | | 27 | |
| | (× 10) | | (× 9) | | (× 6) | |
| DMF | 27,9 | | 14,5 | | 40,5 | |
| | (× 9) | | (× 5) | | (× 9) | |

| | Resin | | | | | |
|---|---|---|---|---|---|---|
| | AM + EBA | | ADE + EBA | | ADE + EBA | |
| Medium | A.βAla.OH | A.βAla.ONa | A.εcap.OH | A.εcap.ONa | A.βAla.OH | A.βAla.ONa |
| Dry | 2,6 | 3,2 | 4,2 | 6,6 | 3,0 | 4,2 |
| Water | 20,8 | 51,2 | 16,8 | 46,2 | 24 | 54,6 |
| | (× 8) | (× 16) | (× 4) | (× 7) | (× 8) | (× 13) |
| $CH_3OH$ | 13 | 17,6 | 21 | 26,4 | 24 | 42 |
| | (× 5) | (× 5,5) | (× 5) | (× 4) | (× 8) | (× 10) |
| $C_2H_5OH$ | 7,8 | 8,0 | 21 | 11,2 | 30 | 25,2 |
| | (× 3) | (× 2,5) | (× 5) | (× 3) | (× 10) | (× 6) |
| $CH_2Cl_2$ | 20,8 | | 50,4 | | 33 | |
| | (× 8) | | (× 12) | | (× 11) | |

TABLE 2-continued

| | VOLUME OF 1 g OF RESIN, in ml. | | |
|---|---|---|---|
| CHCl₃ | 26 | 46,2 | 30 |
| | (× 10) | (× 11) | (× 10) |
| C₅H₅N | 28,6 | 16,8 | 30 |
| | (× 11) | (× 4) | (× 10) |
| DMF | 31,2 | 25,2 | 15 |
| | (× 12) | (× 6) | (× 5) |

The polyacrylamides prepared were tested as cation exchangers in cation exchange chromatography on three substrates:
  two peptide mixtures,
  a mixture of basic proteins (histones from calf thymus).

The peptide mixtures comprise two peptides of the same sequence, only differing by their charge:
Ac Gly Lys Ala Leu Arg Val O Me: 2 charges >0
Ac Gly Lys Ala Leu Arg Val OH: 1 charge >0
Ac Gly Lys Leu Arg Val O Me: 2 charges >0
Ac Gly Lys Leu Arg Val OH: 1 charge >0

These were separated by a sodium chloride gradient with constant pH (pH 5.0, sodium acetate $10^{-2}$ M), using filtered resins corresponding to the following copolymers:
AP +MEBA+A βAla O Na
AP+EBA +A εCap O Na
AP+EBA+A (L) Pro O Na
AP+EBA+A Gly O Na.

Particle size is between 0.1 mm and 0.25 mm. The carboxylic grouping charge is around 0.8 meq/g of dry resin. The chromatograms show a very good separation between the components of the analyzed mixtures.

The calf thymus histones were also subjected to chromatography in a sodium chloride gradient (0 to 2 M). The various components are resolved with a very short analysis time (5 hours), a high rate of elution 80 ml/hour) and a buffer solution (NaCl) better suited to UV analysis.

For a similar reaction, histone ion exchange chromatographies are carried out in sophisticated gradients of guanidinium chloride, with very slow rates and analysis times which may vary between 12 hours and several days (J. BONNER and COLL., "Method in Enzymology", vol. 126, GROSSMAN L. and MALDAVE K., published by Academic Press, New York, 1968).

The resins covered by the invention suitable for use with proteins and also allow easy separation. It should also be noted that the supports described in this paper accept very high rates of elution. It is possible to work up to 300 ml/hour with a column of 1×25 cm.

We claim:
1. New acrylic copolymers comprising:
  from 30% to 90%, by weight, of a monomer (matrix) corresponding to an N-acryloylpolymethylenimine of formula:

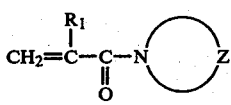

with $R_1$=H or —CH₃

$Z = -(CH_2)_{n1}-$ with $n_1$=4,5 or 6 or

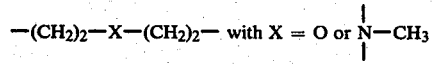

$-(CH_2)_2-X-(CH_2)_2-$ with $X = O$ or $N-CH_3$ or a N-acryloyldialkylamide, of formula:

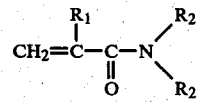

with
$R_1$ having the same meaning as above
$R_2$=—CH₃ or —C₂H₅
from 2% to 50%, by weight, of a monomer (linker) corresponding to an N,N'-diacryloyldiaminoalcane of formula

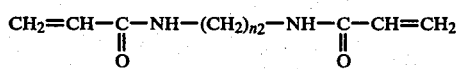

with $n_2$=1 or 2
and from 2% to 65%, by weight, of a monomer (functionalization agent) corresponding to an acryloylaminoacid or ester, racemic of formula:

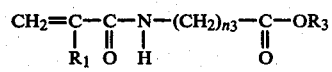

with
$R_1$=H or —CH₃
$R_3$=H or —CH₃
$n_3$=1, 2, 3 or 5
or an asymetric N-acryloylaminoacide (or ester) (L series) of the formula:

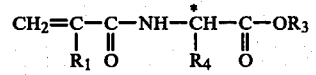

with
$R_1$=H or —CH₃
$R_3$ having the same meaning as above

$R_4 = -CH_3$

—CH(CH₃)₂

—CH₂(CH₃)₂

—(CH₂)₄—NH₂

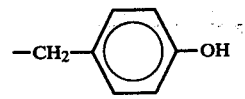

or the N-acryloyl (L) proline, or its methyl ester of the formula:

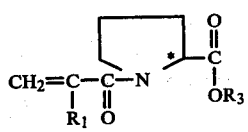

with $R_1$=H or —CH₃

$R_3$ having the same meaning as above.

2. Copolymers according to claim 1 comprising from 70 to 90% of the matrix, from 3 to 10% of the linker and from 10 to 20% of the functionalization agent.

3. Preparation process of copolymers according to claims 1 or 2 consisting in inducing the radical polymerization of the three monomers.

4. Preparation process according to claim 3 consisting in effecting the polymerization in aqueous solution, at a temperature between 0° and 50° C., in the presence of an initiator of radical polymerization.

5. Preparation process according to claim 4, consisting in effecting a polymerization in block in the aqueous solution.

6. Preparation process according to claim 3, consisting in effecting a polymerization in emulsion, in the presence of a non miscible liquid organic phase.

7. Cation exchanger resin consisting essentially of a copolymer as defined in claims 1 or 2.

* * * * *

UNITED STATES PATENT AND TRADEMARK OFFICE
CERTIFICATE OF CORRECTION

PATENT NO. : 4,439,545
DATED : March 27, 1984
INVENTOR(S) : Christian Aspisi et al.

It is certified that error appears in the above-identified patent and that said Letters Patent are hereby corrected as shown below:

Column 6, line 62, delete "NaOCH" and substitute therefor --NaOH--.

Column 7, line 25, delete "60%" and substitute therefor --68%--.

Column 13, line 41, delete "reaction" and substitute therefor --resolution--.

Signed and Sealed this

Eighteenth Day of September 1984

[SEAL]

*Attest:*

*Attesting Officer*

GERALD J. MOSSINGHOFF

*Commissioner of Patents and Trademarks*